United States Patent [19]

Sommadossi et al.

[11] Patent Number: 5,723,449
[45] Date of Patent: *Mar. 3, 1998

[54] METHODS AND COMPOSITIONS FOR INHIBITING URIDINE SECRETION

[75] Inventors: Jean-Pierre Sommadossi; Mahmoud H. el Kouni, both of Birmingham, Ala.

[73] Assignee: The UAB Research Foundation, Birmingham, Ala.

[*] Notice: The term of this patent shall not extend beyond the expiration date of Pat. No. 5,567,689.

[21] Appl. No.: 589,017

[22] Filed: Jan. 19, 1996

Related U.S. Application Data

[63] Continuation of Ser. No. 106,225, Aug. 13, 1993, Pat. No. 5,567,689.

[51] Int. Cl.$^6$ .......................... A61K 31/70; A61K 31/55; C07D 241/04; A01N 43/62
[52] U.S. Cl. .................. 514/50; 514/49; 514/68; 514/218; 514/533
[58] Field of Search .................. 514/49, 50, 68, 514/218, 533

[56] References Cited

U.S. PATENT DOCUMENTS

| | | |
|---|---|---|
| 4,613,603 | 9/1986 | Biziere et al. .......................... 514/242 |
| 4,613,604 | 9/1986 | Chua et al. ............................. 514/274 |
| 4,874,602 | 10/1989 | Calabresi et al. ........................ 424/10 |
| 4,950,466 | 8/1990 | Calabresi et al. ........................ 424/10 |
| 5,064,946 | 11/1991 | Shover et al. .......................... 536/28.2 |
| 5,077,280 | 12/1991 | Sommadossi et al. ................... 514/49 |
| 5,141,943 | 8/1992 | Naguib et al. ........................... 514/270 |
| 5,567,689 | 10/1996 | Sommadossi et al. ..................... 14/50 |

OTHER PUBLICATIONS

"Tissue-specific Enhancement of Uridine Utilization and 5-Fluorouracil Therapy in Mice by Benzylacyclouridine," Darnowski et al., *Cancer Res.* 45:5364–5368 (Nov. 1985).
"Clinical and Pharmacological Study of Orally Administered Uridine," van Groeningen et al., *J. Natl. Cancer. Inst.* 43*6):437–441 (Mar. 20, 1991).
"High-Dose 5-Fluorouacil with Delayed Uridine Rescue in Mice," Martin et al., *Cancer Res.* 42:3964–3970 (Oct. 1982).
"Enhancement of Fluorouracil Therapy By the Manipulation of Tissue Uridine Pools," Darnowski et al., *Pharmac. Ther.* 41:381–392 (1989).
"Use of oral uridine as a substitute for parenteral uridine rescue of 5-fluorouracil therapy, with and without the uridine phosphorylase inhibitor 5-benzyllacyclouridine," Martin et al., *Cancer Chemother. Pharmacol.* 24:9–14(1989).
"Effect of uridine supply on glycogen resynthesis after ischemia in the isolated perfused rat heart," J. Aussedat, *Cardiovasc. Res.* 17:145–151 (1983).
"Anticonvulsant Activities of Δ-8 and Δ-9 Tetrahydrocannabinol and Uridine," Dwivedi et al., *Toxicol. and App. Pharmacol.* 31:452–458 (1975).
"Effects of Nucleosides on Acute Left Ventricular Failure in the Isolated Dog Heart," Buckley et al., *Circulation Res.* VII:847–857 (Nov. 1959).
"Influence of Certain Nucleosides on Glucose Utilization in Man," Elrick et al., *Metabolism* X(1): 46–55 (Jan. 1962).
"The Relationship Between Uracil Nucleotide Concentrations And Glycogen Synthesis in Hepatocytes From Fed And Fasted Rats," Songu et al., *Metabolism* 30(2):119–122 (Feb. 1981).
"Dilazep: an inhibitor of adenosine uptake with intrinsic calcium antagonistic properties," Tonini et al., *J. Pharm. Pharmacol.* 35:434–439 (1983).
"First Report of Management and Outcome of Pregnancies Associated with Hereditary Orotic Aciduria," Bensen et al., *Am. J. Med. Gen.* 41:426–431 (1991).
"Uridine Incorporation in Normal and Ischaemic Perfused Rat Heart," Aussedat et al., *Mol. Phys.* 6:247–256 (1984).
"Benzyllacyclouridine Reverses Azidothymidine-Induced Marrow Suppression Without Impairment of Anti-Human Immunodeficiency Virus Activity," Calabresi et al., *Blood* 76(11):2210–2215 (Dec. 1, 1990).
"Interaction of Uridine with Gaba Binding Sites in Cerebellar Membranes of the Rat," Guarneri et al., *Neurochem. Res.* 8(12):1537–1545 (1983).
"Phase I and Pharmacokinetic Studies of High-Dose Uridine Intended for Rescue from 5-Fluorouracil Toxicity," Leyva et al., *Cancer Res.* 44:5928–5933 (Dec. 1984).
"Enhancement of the Antitumor Activity of 5-Fluorouracil by Uridine Rescue," Klubes et al., *Biochem. Pharmacol.* 26:1585–1591 (1977).
"Interaction Between Uridine and GABA-Mediated Inhibitory Transmission: Studies In Vivo and In Vitro," Guarneri et al., *Epilepsia* 26(6):666–671 (1985).
"Cytidine and Uridine Requirement of the Brain," Geiger et al., *J. Neurochem.* 1:93–100 (1956).
"Effects of Uridine and Inosine on Glucose Metabolism in Skeletal Muscle and Activated Lipolysis in Adipose Tissue," Kypson et al., *J. Pharmacol. and Exptl. Therapeutics* 199(3):565–574 (1976).
"Effect of Cytidine and Uridine on Regeneration of the Liver in Rats Poisoned with Carbon Tetra-chloride," Bushma et al., *Bull. Exptl. Bio. Med.* 88:1480–1483 (1980).
"Effects of Uridine on the Performance and the Metabolism of Oxygenated and Hypoxic Rabbit Hearts," Kypson et al. *J. Mol. Cell. Cardiol.* 10:545–565 (1978).
"Anticonvulsant Effects of Uridine: Comparative Analysis of Metrazol and Penicillin Induced Foci," C.A. Roberts, *Brain Res.* 55:291–308 (1973).
"Metabolic Effects of Inosine and Uridine in Rabbit Hearts and Rat Skeletal Muscles," Kypson, et al., *Biochem. Pharmacol.* 26:1585–1591 (1977).
Jurovcik et al. *Nucl. Acids Res.* 3(8):2143–2154 (1976).

*Primary Examiner*—Gary L. Kunz
*Attorney, Agent, or Firm*—Nutter, McClennen & Fish, LLP

[57] ABSTRACT

Methods and pharmaceutical compositions effective to increase intracellular and plasma uridine concentrations are disclosed. Certain compositions and methods of using such compositions have been found to be effective to inhibit uridine secretion in a subject, thus increasing uridine concentration. Treatments that increase uridine concentrations are useful to combat many treatments and can also be effective in protecting or rescuing uninfected and normal cells that are subject to toxic side effects induced by the administration of certain chemotherapeutic compounds.

13 Claims, No Drawings

METHODS AND COMPOSITIONS FOR INHIBITING URIDINE SECRETION

This application is a continuation application of Ser. No. 08/106,225 filed on Aug. 13, 1993 now U.S. Pat. No. 5,567,689. The contents of all of the aforementioned application(s) are hereby incorporated by reference.

The U.S. Government may have rights in this invention pursuant to NIH Grant No. HL 42125.

BACKGROUND OF THE INVENTION

The present invention relates to methods and pharmaceutical compositions for increasing intracellular and plasma uridine levels, and to methods of treating pathological and physiological disorders that respond to increased intracellular and plasma uridine levels.

Uridine is believed to be a limiting factor in the production of glycogen from glucose in many tissues such as cardiac and striated muscle. Therefore, variations in plasma and intracellular uridine levels can be used to treat many pathological and physiological conditions by supporting tissue metabolic functions. These conditions include, but are not limited to, CNS disorders including cerebrovascular disorders and convulsions, Parkinson's disease, Alzheimer's disease, senile dementia, sleep disorders, muscle dysfunction, lung disorders, diabetes, cardiac insufficiency and myocardial infarction, and liver disease or damage.

Uridine is a naturally occurring nucleoside having a pyrimidine ring structure. This compound is essential in the synthesis of tissue glycogen, such as UDP, UTP, and nucleic acids. Uridine is also known to be useful to treat various physiological and pathological conditions. For example, uridine has been shown to increase myocardial performance, glucose uptake, glycogen synthesis and the breakdown of ATP in heart tissue of rabbits (Kypson et al., *Biochem, Pharm.*, 26:1585–1591, 1977, and Kypson et al., *J. Mole. and Cell. Cardiology*, 10:545–565, 1978). Uridine has also been shown to increase myocardial contractility in the hearts of frogs, rats (Aussedate, *J. Cardiovascular Research,*. 17:145–151, 1983) and dogs (Buckley et al., *Circulation Research*, Vol. VII, 1959). Increases in plasma uridine levels can be of particular benefit to patients who suffer from hypoxic or ischemic heart tissue since stimulated gycolysis and glyeogenolysis are important compensatory mechanisms in heart hypoxia. These benefits could result from uridine's role as a substrate of enzymes such as UDP-glucose pyrophosphorylase and UDP-glucose glycogen transglucosylase or due to an increase of tissue uridine nucleotides such as UTP, UDP or UMP. Alternatively, the increased activity may be due to the presence of an intermediate in glycogen synthesis, UDP-glucose. It is believed that glycolytic ATP has a major role in preserving membrane structure after a prior period of ischemia and that uridine is necessary for the increased glycolysis that produces ATP during the recovery period.

Plasma uridine level fluctuations also have important implications in muscle performance. Uridine has been found to increase glucose uptake and glycogen synthesis in isolated rat skeletal muscle (Kypson et al., 9177). These increases in metabolism occur at low concentrations of uridine ($10^{-4}$M), thus indicating that the effects may be receptor-mediated. The ability to maintain levels of uridine, thus avoiding overloading the targeted receptors, could be most useful in maintaining proper muscle performance Uridine levels are also important in central nervous system functioning. The presence of uridine and cytidine in the blood has been shown to be necessary for normal brain function in experiments with isolated cat brain (Geiger et al., *J. Neurochem.*, 1:92–100, 1956). Electrical activity has been shown to cease after about one hour in an isolated brain perfused with a simple blood medium, but electrical activity is restored by the addition of uridine and cytidine. Corneal and pupillary reflexes also return to normal upon the addition of uridine and cytidine to the perfused media. These effects are believed to be due to improved carbohydrate metabolism rather than to increased oxygen consumption or blood flow.

Further, epilepsy and seizures are related to a deficiency in the inhibitory neurotransmitter, gamma-aminobutyric acid (GABA). Binding studies of uridine with the GABA receptor of cerebellar membranes as well as receptors in those areas of the brain closely associated with convulsions, indicate that uridine may have an agonist effect on the receptor. That is, uridine, upon binding the GABA receptor may have an inhibitory response in neurotransmission (Guarneri et al., *Neurochem, Research*, 8:12, 1983). Therefore, the control of intracellular and plasma uridine levels could have important implications in the treatment of CNS disorders, including cerebrovascular disorder and convulsions, epilepsy, Parkinson's and Alzheimer's diseases, and senile dementias.

Another aspect uridine is its potential use in the treatment of liver damage and hepatitis. Uridine has been shown to normalize conjugating and excretory functions in $CCl_4$ damaged rat livers (Bushma et at., *Bull. Exptl. Biol. Med.*, 88:1480–1483, 1989).

Uridine can also be used in the treatment of genetic deficiencies in the pyrimidine synthetic pathway. Uridine administration has been effective to manage patients with hereditary orotic aciduria, (Bensen et al., *Am. J. Med Gen.*, 41:426–431, 1991).

The control of plasma uridine levels can also play a major role in the treatment of retroviral diseases and cancer. Acquired immune deficiency syndrome (AIDS) is generally accepted to be the result of infection with a type of retrovirus termed the human immunodeficiency virus (HIV). A number of strains or classes or HIVs have recently been identified, and it appears that HIVs are part of a broader family of retroviruses having similar genomes that are responsible for a wide range of disease with diverse clinical manifestations.

Present management of patients with HIV infections typically involves the administration of a therapeutic agent such as pyrimidine nucleoside analogue, for example, 3'-azido-3'-deoxythymidine ("AZT"). Such chemotherapeutic agents function by inhibiting the HIV reverse transcriptase and reducing the cytopathic effects, including the suppression of bone marrow cell growth in the patient. This complication often limits the dosage or duration of therapy that can be implemented. One of the major limitations of various antiretroviral (e.g., AZT) and anticancer (e.g. 5-fluorouracil, ("5-FU") and 5-fluoro-2'-deoxyuridine ("FdUrd")) pyrimidine analogues has been this myelosuppression. Complete protection (and reversal) from this toxicity can be achieved in vitro and in vivo by administration of uridine.

Unfortunately, however, the effective elevation of uridine levels in patients has proved difficult. Therefore, treatments based on the known utility of raised plasma uridine levels for the above-mentioned conditions and others have not heretofore been practical. Although uridine is present in blood plasma of different species in relatively high and constant concentrations (1–5 μM), its half life in the plasma is approximately 2 minutes. Uridine entering the liver is rapidly degraded to uracil by hepatic uridine phosphorylase (UrdPase). More than 90% of the plasma uridine entering the liver by the portal vein is degraded in single pass while constant amounts of uridine from de novo biosynthesis are released into the hepatic vein blood. In clinical trials administration several times per day of high doses of uridine (1 to 3 gm/m$^2$) is required to overcome its rapid degradation and to achieve the plasma uridine concentrations required to protect the patients from, for example, toxicity that is induced by the therapeutic agents. With these high doses, rapid elimination of uridine from the plasma is observed, and urinary excretion of uridine constitutes 15–40% of the dose. Uracil is also elevated in the plasma of those individuals receiving high doses of uridine and is excreted as 2–17% of the dose. Furthermore, the use of high doses of uridine is hampered by its toxic side effects including phlebitis, pyrogenic reactions and diarrhea.

Uridine phosphorylase inhibitor (UPIs), which prevent the phosphorylization of uridine to uracil in the liver, have also been shown to increase the uridine pool. However, it is believed that much of the increased uridine resulting from the administration of UPIs is passed in the urine, therefore achieving no real accumulation of intracellular or plasma uridine.

Accordingly, there exists a need for treatment methods and pharmaceutical compositions that effectively and safely enable the control of intracellular and plasma uridine levels.

It is thus an object of the invention to provide methods to effectively and safely increase intracellular and plasma uridine levels to treat certain pathological and physiological conditions. Another object is to provide methods to increase intracellular and plasma uridine levels to protect against and to reverse the toxic side effects of certain chemotherapeutic agents. A further object is to provide pharmaceutical compositions that are effective to safely increase intracellular and plasma uridine levels. Other objects will be apparent to those of ordinary skill the art from the following disclosure.

SUMMARY OF THE INVENTION

According to the present invention a method is provided to increase intracellular and plasma uridine levels by administering to a patient compounds that inhibit secretion of uridine. The uridine secretion inhibiting compounds can be compounds having the following formula and pharmaceutically acceptable salts of such compounds:

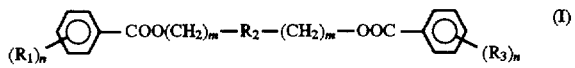

where:

R$_1$ and R$_3$ are lower alkoxy groups having from 1 to 3 carbon atoms, and may be the same or different, n is an integer from 1 to 3, m is 2 or 3, R$_2$ is

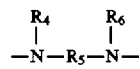

where R$_4$ and R$_6$ are methyl, ethyl or propyl, and may be the same or different, and R$_5$ is methyl, ethyl, propyl or butyl; or where R$_2$ is

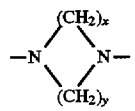

where x is an integer from 2 to 4 and y is 2 or 3, and the sum of x and y is from 5 to 7. Suitable compounds that inhibit uridine secretion can also be compounds that compete with uridine in the renal transport mechanisms of uridine. Such uridine competing compounds include L-uridine, L-2', 3'-dideoxyuridine, and D-2',3'-dideoxyuridine. Uridine secretion inhibiting compounds of the type noted above may be administered alone or with other compounds capable of increasing available uridine, such as uridine, cytidine, prodrugs of uridine or cytidine, uridine nucleotides, cytidine nucleotides, prodrugs of these nucleotides, uridine and cytidine dimers, uridine phosphorylase inhibitors, and homo- or hetero- dimers of specific dideoxynucleoside compounds and/or uridine, cytidine, and uridine phosphorylase inhibitors.

The uridine secretion inhibiting compounds may also be administered with certain therapeutic agents that produce toxic side effects in healthy cells. Such therapeutic agents include analogues of pyrimidine nucleoside analogs (e.g., AZT; FdUrd) and pyrimidine bases (5-FU).

In another aspect, the invention encompasses pharmaceutical compositions that are effective to increase intracellular and plasma uridine levels. These can be combinations of compounds that inhibit uridine secretion, or salts thereof, with other compounds that can increase available uridine, such as uridine, cytidine, prodrugs of uridine or cytidine, uridine nucleotides, cytidine nucleotides, prodrugs of these nucleotides, uridine phosphorylase inhibitors, and homo- or hetero- dimers of specific dideoxynucleoside compounds and/or uridine, cytidine, and uridine phosphorylase inhibitors. The pharmaceutical compositions can further include therapeutic agents.

Given the known role of uridine in the proper functioning of respiratory and muscular systems, the present invention can have utility in treating disorders of the heart, such as myocardial infarction or cardiac insufficiency, as well as disorders of the lungs or the muscles. Also, the present invention could be of use in treating liver disorders such as liver disease, liver damage, or hepatitis. Finally, due to the fact that uridine has been used to manage patients with hereditary orotic aciduria, the treatment methods embodied herein are anticipated to have utility in treating such an ailment.

In one aspect of the invention, a treatment for retroviral diseases, including AIDS, is disclosed in which a pyrimidine nucleoside analogue, such as AZT, is administered with a uridine secretion inhibiting compound to treat the infection and to protect or rescue uninfected cells from toxicity caused by the pyrimidine nucleoside analog. Other compounds that increase available uridine, such as those noted above, can also be administered with these compounds.

DETAILED DESCRIPTION OF THE INVENTION

The present invention concerns methods and compositions for increasing intracellular and plasma uridine levels in a subject. Maintaining and/or increasing plasma and intracellular uridine levels can be useful to treat a variety of pathological and physiological conditions including CNS disorders, Parkinson's disease, Alzheimer's disease, senile dementia, sleep disorders, muscle dysfunction, lung disorders, diabetes, cardiac insufficiency and myocardial infarction, liver disease, and liver damage. The increase of plasma and intracellular uridine levels is also important in preventing or reversing damage to healthy cells caused by the administration of chemotherapeutic agents such as analogues of pyrimidine bases (e.g., 5-fluorouracil) and pyrimidine nucleosides (e.g., AZT).

As noted above, plasma uridine is rapidly degraded upon entering the liver. Administration of uridine or other compounds that increase plasma uridine concentration are not necessarily effective to maintain increased plasma uridine levels as a substantial amount of the added uridine is lost through urinary excretion.

The invention recognizes that intracellular and plasma uridine levels in a subject can be increased by administering to a subject an effective uridine secretion inhibiting compound. The term "uridine secretion inhibiting compound" refers to compounds that are effective to increase the intracellular and plasma concentration of uridine. These compounds generally act to inhibit the transport of uridine across cell membranes from the interior of the cell to the exterior of the cell. More specifically, these compounds are believed to inhibit the renal clearance of uridine. Other compounds that limit the amount of uridine secreted, such as by competition with uridine, can also be considered uridine secretion inhibiting compounds.

Suitable uridine secretion inhibiting compounds can be compounds having the following formula and pharmaceutically acceptable salts of such compounds.

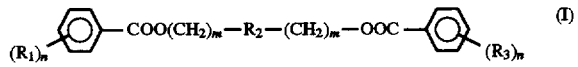  (I)

where:

R$_1$ and R$_3$ are lower alkoxy groups having from 1 to 3 carbon atoms, and may be the same or different, n is an integer from 1 to 3, m is 2 or 3, R$_2$ is

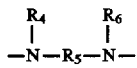

where R$_4$ and R$_6$ are methyl, ethyl or propyl, and may be the same or different, and R$_5$ is methyl, ethyl, propyl or butyl; or where R$_2$ is

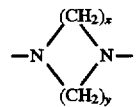

where x is an integer from 2 to 4 and y is an integer from 2 to 3, and the sum of x and y is from 5 to 7. Examples of preferred uridine secretion inhibiting compounds having the above general formula include dilazep (N,N'-bis[3-(3,4,5-trmethoxybenzoyloxy)propyl] homopiperazine) and hexobendine (N,N'-dimethyl)-N,N'-bis[3-(3',4', 5'-trimethoxybenzoxy)propyl] ethylenediamine).

Other compounds useful to inhibit uridine secretion are compounds that compete with uridine in the renal transport mechanisms of uridine. Such compounds include L-uridine; L-2'-3'-dideoxyuridine; and D-2'3'-dideoxyuridine.

Uridine secretion can be inhibited by administering compounds of the type noted above by Formula (I) or by administering the uridine competing compounds noted above. Uridine secretion inhibiting compounds of the type denoted by Formula (I) typically are administered at preferred doses in the range of about 1 to 5 mg/kg of body weight 2 to 3 times per day. Uridine competing compounds preferably are administered at doses ranging from 5 to 50 mg/kg of body weight 2 to 3 times per day. Indeed, it has been found that the administration of dilazep to Rhesus monkeys at 1 to 2 mg/kg of body weight per day results in a 7 to 8-fold increase in plasma uridine levels without apparent toxicity. Moreover, such treatment increases by about 4 to 5-fold, the plasma half-life of uridine. These uridine levels are roughly equivalent to those obtained by administering high doses of uridine (1 to 3 g/m$^2$ per day), without the toxic side effects associated with uridine administration.

Uridine levels can also be increased or maintained by coadministering or sequentially administering with uridine secretion inhibiting compounds, compounds that inhibit uridine phosphorylase, and thus increase the available uridine pool. Suitable uridine phosphorylase inhibiting compounds include benzylacyclouridine (BAU); benzyloxybenzylacyclouridine (BBAU); aminomethylbenzylacyclouridine (AMBAU); aminomethylbenzyloxybenzylacyclouridine (AMB-BAU); hydroxymethyl-benzylacyclouridine (HMBAU); and hydroxymethyl-benzyloxybenzylacyclouridine (HMBBAU). Additional suitable uridine phosphorylase inhibitors and methods for synthesizing such compounds are disclosed in the following references, all of which are hereby incorporated by reference: U.S. Pat. No. 4,613,604 (Chu, et al.), Niedzwicki, et al. Vol. 30, *Biochemical Pharmacology* pp. 2097–2101 (1981); Niedzwicki, et al., Vol. 31, *Biochemical Pharmacology* pp. 1857–1861 (1982); Lin, et al. Vol. 25 *J. Med. Chem.* pp. 971–973 (1985); and U.S. Pat. No. 5,077,280 (Sommadossi, et al.). Derivatives of 5-benzyl barbiturate can also be used to inhibit uridine phosphorylase. Such compounds, as are described in U.S. Pat. No. 5,141, 943 (Naguib, et al.), which is incorporated herein by reference, include 5-benzyloxybenzyl barbiturate; 5-benzyloxybenzyl-1-[(1-hydroxy-2-ethoxy)methyl] barbiturate; 5-benzyloxybenzylacetyl-1-[(1-hydroxy-2-ethoxy) methyl] barbiturate; 5-benzyloxybenzyl-1-[(1,3-dihydroxy-2-propoxy)methyl] barbiturate; 5-benzyloxybenzyl-1-[1-hydroxy, 3-amino-2-propoxy)methyl] barbiturate; 5-benzyloxybenzyl-1-[(2-(3-carboxypropionyloxy)ethoxy) methyl] barbiturate; 5-benzyl-1-[(1-hydroxy-2-ethoxy) methyl] barbiturate; 5-methoxybenzylacetyl barbiturate; 5-benzyl-1-[(1,3-dihydroxy-2-propoxy)methyl] barbiturate; 5-benzyl-1-[(1-hydroxy, 3-amino-2-propoxy)methyl] barbiturate; and 5-benzyl-1-[(2-(3-carboxypropionyloxy)ethoxy) methyl] barbiturate.

Acyclouridines, used as uridine phosphorylase inhibiting compounds, can be administered according to the invention at 5 to 200 mg/kg/day. Preferred dosages for 5-benzyl barbiturate compounds administered according to the invention are in the range of 5 to 200 mg/kg/day.

In addition, the benefits of exogenous uridine can be realized by administering certain prodrugs. Suitable compounds include prodrugs of uridine and cytidine (e.g., triphenyluridine and triphenylcytidine); prodrugs of uridine 5'-monophosphate (UMP) and cytidine 5'-monophosphate (CMP) (e.g., mono- and di-alkyl esters, acyloxyalkyl esters, alkoxycarbonylmethyl esters, substituted ethyl and propyl esters, amidomethyl esters, benzyl esters phenyl esters, phosphonamidates, cyclophosphate esters); uridine and cytidine homodimers and their esters (e.g., U-P-U, U-P-C, C-P-C, and isomers thereof); homodimers of uridine phosphorylase inhibitors; and heterodimers of dideoxynucleoside compounds and uridine, cytidine, or uridine phosphorylase inhibitors (e.g., AZT-P-U and AZT-P-BAU). Similarly, uridine and cytidine nucleotides and prodrugs of these nucleotides may be administered.

Prodrugs of uridine and cytidine and their nucleotides, are believed to be useful as they improve the bioavailablility of uridine or cytidine by enhancing their lipid solubility and transport across the cell membrane. This serves to prevent premature degradation of uridine and cytidine. Nucleotide prodrugs are particularly useful because the negative charge of nucleotides prevents their passage through cell membranes. Masking the charge through a prodrug will facilitate transport of the nucleotides across the cell membranes. Once inside the cell, cellular esterases can unmask the negative charge, causing the nucleotide to be trapped within the cell to be available for further nucleotide synthesis.

Some chemotherapeutic agents can be useful to treat diseases, but can also cause serious side effects that can limit their use and/or effectiveness. Examples of such agents are pyrimidine bases (e.g., 5-fluorouracil) used in the treatment of cancers, and pyrimidine nucleosides (e.g., AZT) used in the treatment of AIDS.

Pyrimidine nucleoside analogues are known to inhibit viral replication when administered in amounts ranging from about 10 mg to about 100 mg per kilogram of body weight per day, depending upon the potency and toxicity of the particular analogue. Such dosage units are employed so that a total of from about 0.7 to about 7 grams of the nucleoside analogue are administered to a subject of about 70 kg of body weight in a 24-hour period. For example, one presently accepted protocol for AZT treatment calls for 200 mg of AZT to be administered three times per day. 5-fluorouracil, a pyrimidine base, can be administered at therapeutic dosages as are known to those skilled in the art.

Examples of pyrimidine nucleoside analogues useful with the present invention include 3'-azido-3'-deoxythymidine; 3+fluoro-3'-deoxythymidine; 3'-dideoxycytidin-2'-ene; and 3'-deoxy-3'-deoxythymidin-2'-ene.

Chemotherapeutic agents of the type noted above may be coadministered or sequentially administered with the uridine secretion inhibiting compounds of the invention. Moreover, the chemotherapeutic agents and uridine secretion inhibiting compounds can be administered with uridine phosphorylase inhibitors or prodrugs or uridine and cytidine or the nucleotides.

Dosages preferably are adjusted to raise a subject's plasma uridine levels to 50 µM to 100 µM at steady state.

The dosage regimen of the combination therapies described above may be adjusted to provide the optimum therapeutic response. For example, several divided doses may be administered daily or the dose may be proportionally reduced as indicated by the exigencies of the therapeutic situation.

A decided practical advantage is that the active compounds may be administered in any convenient manner, such as by the oral, intravenous, intramuscular, or subcutaneous routes.

The active compounds disclosed herein may be orally administered, for example, with an inert diluent or with an assimilable edible carrier. They may also be enclosed in hard or soft shell gelatin capsule, or they may be compressed into tablets, or incorporated directly into food. For oral therapeutic administration the active compounds may be incorporated with excipients and used in the form of ingestible tablets, bucal tablets, troches, capsules, elixirs, suspensions, syrups, wafers and the like. The amount of active compounds is such therapeutically useful compositions is such that suitable dosage will be obtained.

The tablets, troches, pills, capsules and the like may also contain the following: a binder, such as gum tragacanth, acacia, cornstarch, or gelatin; excipients, such as dicalcium phosphate; a disintegrating agent, such as corn starch, potato starch, aliginic acid and the like; a lubricant, such as magnesium stearate; and a sweetening agent, such as sucrose, lactose or saccharine; and a flavoring agent, such as peppermint, oil or wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compounds, sucrose as a sweetening agent, methyl and propylparabens as preservatives, a dye and a flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof, and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions or manufacture and storage and must be preserved against the contaminating action of microorganisms, such a bacteria and fungi. The carrier can be a solvent or dispersion medium containing for example, water, ethanol, glycerol, propylene glycol, and polyethylene glycol, and vegetable oils. The proper fluidity can be maintained, for example, by the use of a coating such as a lecithin, by the maintenance of the required particle size in the case of dispersions and by the use of surfactants. Various antibacterial and antifungal agents (e.g., parabens, chlorobutanol, phenol, sorbic acid, thimerosal) can be used to prevent the action of microorganisms. In many cases, it will preferably to include isotonic agents, or example, sugars or sodium chloride. Prolonged absorption the injectable compositions can be brought about by the use in the compositions of agents that delay absorption, for example, aluminum monostearate and gelatin.

Sterile injectable solutions can be prepared by incorporating the active compounds in the required amount in the appropriate solvent with various of the other ingredients enumerated above, as required, followed by filtered sterilization. Generally, dispersions can be prepared by incorporating the various sterilized active ingredients into a sterile vehicle which contains the basic dispersion medium and the required as well as additional ingredients of the type enumerated above. Sterile powders used to prepare sterile injectable solutions can be prepared by vacuum-drying and freeze-drying techniques.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art.

It should be clear that various modifications, additions and subtractions can be made without departing from the spirit or scope of the invention. For example, it should be appreciated that the present invention can also be employed in conjunction with other chemotherapeutic agents or biological response-modifying agents. For example, the combination therapy of the present inventions can be employed in tandem with the administration of bone marrow stimulating factors, such as granulocyte-macrophage colony stimulating factors (GM-CFSs), other colony stimulating factors, erythropoietin (EPO) and other compounds that stimulate hematopoietic activity. (For a further discussion of GM-CSF activity, see Hammer et al. Vol, 31 *Antimicrogial Agents and Chemotherapy*, pp. 1046–1050 (1987)). Similarly, the combination therapy of the present invention can be undertaken in conjunction with efforts to stimulate the immune system, such as by the administration of interferons (e.g., alpha-A inteferon) or other lymphokines.

The invention is further illustrated by the following non-limiting examples.

EXAMPLES

The dilazep used in the following examples was obtained from commercial sources. The chemical purity of the compound was confirmed by mass spectrum and/or HPLC analysis to be greater than 99%. Non-labeled uridine was purchased from Sigma Chemical Co. (St. Louis, Mo.). [5-$^3$H]-uridine (28 Ci/μmol) was purchased from Moravek Biochemicals (Brea, Calif.) and was of greater than 99% purity as ascertained by HPLC. All other chemicals used in the examples were of the highest quality commercially available.

Young adult rhesus monkeys (*Macaca mulatta*), weighing between 4.26 and 6.24 kg, used for the studies were maintained at Yerkes Regional Primate Research Center of Emory University in accordance with the guidelines established by the Animal Welfare Act and the National Institutes of Health Guide for the Care and Use of Laboratory Animals.

Example 1

Single dose of Uridine and effect of Dilazep

The monkeys received one subcutaneous trace dose of 500 μCi [5-$^3$H]-uridine with uridine at either 25 mg/kg of body weight or 83.3 mg/kg of body weight. The uridine was administered both with and without dilazep. When dilazep was given it was administered at either 1 or 2 mg/kg of body weight, dissolved in sterile phosphate-buffed saline (pH 7.4). Samples of blood (3 ml) were collected in heparinized tubes at 0, 5, 10, 15 and 30 minutes and 1, 2, 4 and 6 hours after injection. When possible, urine was also collected by cytocentesis at similar time intervals. The plasma and urine samples were frozen at −20° C. until analysis.

Single dose of dilazep

Monkeys received a subcutaneous dose of 1 or 2 mg/kg of dilazep, dissolved in sterile phosphate-buffered saline (pH 7.4). Samples of blood (3 ml) were collected in heparinized tubes at 0, 15 and 30 minutes, and 1, 2, 4, 6 and 24 hours after injection. When possible, uridine was collected at similar time intervals by cytocentesis. The plasma and urine samples were frozen at −20° C. until analysis.

Analysis of Samples

Nonradioactive samples (500 μl) of plasma were extracted with 1 ml of 15% ice cold trichloroacetic acid. The proteins were removed by centrifugation, and sample temperature was maintained at 5° C. The supernant was removed and an equivalent amount of a 1:1 mixture of ice cold trioctylamine and 1,1,2-trichlorotrifluoroethane (freon) was added. The phases were allowed to separate and 50 μl aliquots of the top phase were analyzed by HPLC using a Hewlett-Packard Model 1050 Liquid Chromatograph equipped with a manual injector and a fixed wavelength spectrophotometer. Reversed-phased chromatography was performed using a Hypersil ODS 5 μm column (Jones Chromatography, Littleton, Colo.). Urine samples were filtered through a 0.45 μm pore size Acro LC 13 filter (Gelman Sciences, Ann Arbor, Mich.) to remove proteins and 50 μl aliquots were analyzed by HPLC. Isocratic elution was performed at 1 ml/min with 10 mM phosphoric acid and 10 μM heptane sulfonic acid (pH 3.1). Column temperature was maintained at 25° C., and the absorbance was measured at 254 nm. Under these conditions, uridine eluted at 14–15 min, uracil at 10–12 min, and dihydrouracil at 8–9 min. Radioactive eluent from the column was directed via a low dead-volume connection line into a model 2112 Redirac fraction collector (LKB Instruments, Rockville, Md.), and timed fractions of 0.5 ml were collected into miniscintillation vials. After adding 5 ml of Econo-Safe scintillation fluor (Research Products International Corp., Mount Prospect, Ill.), radioactivity was measured by using Beckman Model LS 5000TA liquid scintillation counter (Beckman Instruments, Inc., Fullerton, Calif.) equipped with an automatic quenching correction program. Intra- and inter- day percentage coefficients of variation were less than 10%, at concentrations between 4 and 400 μM. The detection limits were 2.0 μM.

Pharmacokinetic Analysis

The pharmacokinetic parameters of uridine was estimated by compartmental model-independent methods using a SIPHAR/Base program. The AUC was determined by the trapeziodal rule with extrapolation to time infinity using the terminal disposition slope (K) generated by a weighted nonlinear least-squares regression of an exponential fit of the data, with the weighted square factor set as the reciprocal of the calculated concentration squared. Elimination half-life of uridine was calculated from 0.693/K. The total plasma clearance (Cl) was calculated by dividing the dose by the AUC and the weight of the monkey. The peak plasma concentration ($C_{max}$) values and time to peak plasma concentration ($T_{max}$) values were observed experimental values. Renal clearance ($CL_R$) of uridine was calculated by dividing the dose by the AUC. The data obtained are illustrated below in Tables 1 and 2.

TABLE 1

Pharmacokinetic Parameters of Uridine after Subcutaneous Administration of Dilazep ± Uridine in Rhesus Monkeys

| Monkey | $C_{max}$* (μM) | $C_{max}/C_o$ | $T_{max}$ (h) | AUC (μmol × h/L) | $CL_R$ (mL/h/kg) |
|---|---|---|---|---|---|
| 83.3 mg/kg uridine | | | | | |
| Rou-1 | 175.0 | 10.7 | 0.5 | 369.5 | 67.2 |
| 1 mg/kg Dilzazep | | | | | |
| Rcf-2 | 102.4 | 6.6 | 4.0 | 498.4 | 1.4 |
| 1 mg/kg Dilazep + 25 mg/kg uridine | | | | | |
| RSe-2 | 327.6 | 22.2 | 1.0 | 749.2 | 2.8 |
| 2 mg/kg Dilazep | | | | | |
| CF-77 | 19.0 | 7.7 | 1.0 | 71.4 | 8.8 |
| 2 mg/kg Dilazep + 83.3 mg/kg Uridine | | | | | |
| RA1-1 | 305.0 | 39.1 | 0.5 | 865.8 | 0.95 |

*$C_{max}$ is peak plasma concentration; $C_{max}/C_o$ is peak plasma concentration over plasma concentration at t = 0; $T_{max}$ is time to peak plasma concentration; AUC is area under the curve, $CL_R$ is renal clearance of uridine

TABLE 2

Pharmacokinetic Parameters of Uridine after Subcutaneous Administration of 1 mg/kg Dilazep and 25 mg/kg Uridine

| Monkey | $C_{max}$* (µM) | $C_{max}/C_0$ | $T_{max}$ (hr) | AUC (µmol × h/L) | $Cl_R$ |
|---|---|---|---|---|---|
| RYy-2 | 129.5 | 20.3 | 1 | 228.3 | NA |
| ROy-2 | 112.0 | 5.4 | 0.5 | 420.8 | NA |
| RFu-2 | 87.7 | 42.8 | 0.75 | 334.8 | NA |
| RGu-2 | 197.3 | 14.0 | 0.25 | 343.5 | NA |

*$C_{max}$ is peak plasma concentration; $C_{max}/C_0$ is peak plasma concentration over plasma concentration at t = O; $T_{max}$ is time to peak plasma concentration; AUC is area under the curve, $Cl_R$ is renal clearance of uridine; NA: Not available.

All publications and patents referenced above are hereby incorporated by reference in their entirety.

It is understood that various modifications may be made with the invention described and claimed herein without departing from the intended scope. Moreover, the invention encompasses the use of all formulations of active ingredients and chemotherapeutic agents referenced herein, including immediate release and sustained release formulations.

What is claimed is:

1. A method for protecting and/or rescuing normal or uninfected cells from toxicity resulting from the administration of a chemotherapeutic agent to a patient comprising:
   (a) administering an anticancer agent selected from the group consisting of a pyrimidine base and a pyrimidine nucleoside analogue; and
   (b) administering an amount of a uridine secretion inhibiting compound effective to increase plasma and intracellular uridine levels, the uridine secretion inhibiting compound being represented by compounds having the following formula and pharmaceutically acceptable salts thereof:

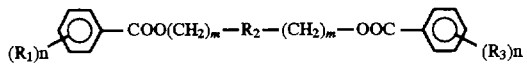

where:

$R_1$ and $R_3$ are lower alkoxy groups having from 1 to 3 carbon atoms, and are the same or different, n is an integer from 1 to 3, m is 2 or 3, $R_2$ is

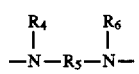

where $R_4$ and $R_6$ are methyl, ethyl or propyl, and are the same or different, and $R_5$ is methyl, ethyl, propyl or butyl; or where $R_2$ is

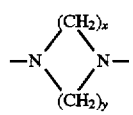

where x is an integer from 2 to 4 and y is 2 or 3, and the sum of x and y is from 5 to 7.

2. The method of claim 1 wherein the pyrimidine nucleoside analogue is selected from the group consisting of 3'-fluoro-3'deoxythymidine, 5-fluoro-2'deoxyuridine and derivatives thereof, and the pyrimidine base is 5-fluorouracil.

3. The method of claim 1 wherein the uridine secretion inhibiting compound is selected from the group consisting of dilazep and hexobendine.

4. The method of claim 3, wherein the uridine secretion inhibiting compound is administered at a dosage of about 1 to 5 mg per kg of body weight two to three times per day.

5. The method of claim 1 further comprising the step of administering to the patient one or more compounds selected from the group consisting of uridine phosphorylase inhibitors, uridine, cytidine, prodrugs of uridine, prodrugs of cytidine, and heterodimers of dideoxynucleoside analogues and uridine, cytidine or uridine phosphorylase inhibitors, wherein the heterodimers are selected from the group consisting of 3', 5'-phosphodiester dimers and 5', 5'-phosphodiester dimers.

6. The method of claim 1 further comprising the step of administering to the patient, in an amount effective to increase intracellular and plasma uridine levels, a uridine secretion inhibiting compound that competes with uridine in the renal transport mechanism of uridine and is selected from the group consisting of L-uridine, L-2,3'-dideoxyuridine, and D-2',3'-dideoxyuridine.

7. The method of claim 5 wherein the prodrugs of uridine are uridine homodimers and their esters, and wherein the homodimers are selected from the group consisting of 3', 5'-phosphodiester dimers and 5', 5'-phosphodiester dimers.

8. The method of claim 5 wherein the prodrugs of cytidine are cytidine homodimers and their esters, and wherein the homodimers are selected from the group consisting of 3', 5'-phosphodiester dimers and 5', 5'-phosphodiester dimers.

9. A method for protecting and/or rescuing normal or uninfected cells from toxicity resulting from the administration of a chemotherapeutic agent to a patient comprising administering to the patient:
   (a) 5-fluorouracil; and
   (b) an amount of a uridine secretion inhibiting compound effective to increase plasma and intracellular uridine levels, the uridine secretion inhibiting compound being represented by compounds having the following formula and pharmaceutically acceptable salts thereof:

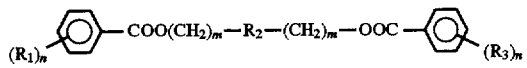

where:

$R_1$ and $R_3$ are lower alkoxy groups having from 1 to 3 carbon atoms, and may be the same or different, n is an integer from 1 to 3, m is 2 or 3, $R_2$ is

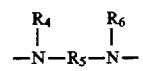

where $R_4$ and $R_6$ are methyl, ethyl or propyl, and may be the same or different, and $R_5$ is methyl, ethyl, propyl or butyl; or where $R_2$ is

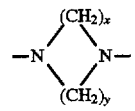

where x is an integer from 2 to 4 and y is 2 or 3, and the sum of x and y is from 5 to 7.

10. A method for protecting and/or rescuing normal or uninfected cells from toxicity resulting from the administration of a chemotherapeutic agent to a patient comprising administering to the patient an anticancer agent selected from the group consisting of a pyrimidine base and a pyrimidine nucleoside analogue, and a uridine secretion inhibiting compound that competes with uridine in the renal transport mechanism of uridine and is selected from the group consisting of L-uridine, L-2,3'-dideoxyuridine, and D-2',3'-dideoxyuridine in an amount effective to increase intracellular and plasma uridine levels.

11. The method of claim 1 wherein the pyrimidine base or pyrimidine nucleoside analogue is a fluorinated compound.

12. The method of claim 10 wherein the pyrimidine base or pyrimidine nucleoside analogue is a fluorinated compound.

13. The method of claim 10 wherein the pyrimidine nucleoside analogue is selected from the group consisting of 3'-fluoro-3'deoxythymidine, 5-fluoro-2'deoxyuridine and derivatives thereof, and the pyrimidine base is 5-fluorouracil.

* * * * *